United States Patent [19]
Walsdorf et al.

[11] Patent Number: 5,344,389
[45] Date of Patent: Sep. 6, 1994

[54] COMBINATION SEAL AND CONSTRICTING DEVICE

[75] Inventors: Neill B. Walsdorf; Dan K. Crawford; Perry W. Nadig, all of San Antonio, Tex.

[73] Assignee: Mission Pharmacal Company, Inc., San Antonio, Tex.

[21] Appl. No.: 890,446

[22] Filed: May 28, 1992

Related U.S. Application Data

[63] Continuation-in-part of Ser. No. 643,898, Jan. 22, 1991, abandoned.

[51] Int. Cl.$^5$ .............................................. A61F 5/41
[52] U.S. Cl. ........................................ 600/41; 600/39
[58] Field of Search .............................. 600/38, 39, 41

[56] References Cited

U.S. PATENT DOCUMENTS

| | | |
|---|---|---|
| 1,225,341 | 5/1917 | Lederer . |
| 1,608,806 | 11/1926 | Nelson ................................ 600/41 |
| 3,759,253 | 9/1973 | Cray . |
| 4,378,008 | 3/1983 | Osbon, Sr. . |
| 4,539,980 | 9/1985 | Chaney . |
| 4,628,915 | 12/1986 | Chaney ................................ 600/41 |
| 4,641,638 | 2/1987 | Perry ................................ 600/39 |
| 4,872,462 | 10/1989 | Salz et al. . |

FOREIGN PATENT DOCUMENTS 347300 8/1960 Switzerland .

*Primary Examiner*—Cary E. O'Connor
*Attorney, Agent, or Firm*—Ross, Howison, Clapp & Korn

[57] ABSTRACT

A combination seal and constricting device and method of use for the external treatment of impotence is provided. The subject device is made of a pliable elastomeric material and is characterized by a centrally disposed cylindrical collar connected at one end thereof to a radially extending skirt having a forwardly facing, annular, elastomeric seating and sealing surface and a rearwardly facing surface substantially flush with one end of said collar. When used in combination with a conventional vacuum erection device, the combination seal and constricting device is positioned at the open end of the evacuation cylinder of the conventional vacuum erection device with the radially extending skirt flush between the open end of the cylinder and the user's groin. In this position, the subject device aids in establishing and maintaining a substantially airtight seal around the open end of the cylinder and the base of the penis during evacuation pumping.

20 Claims, 3 Drawing Sheets

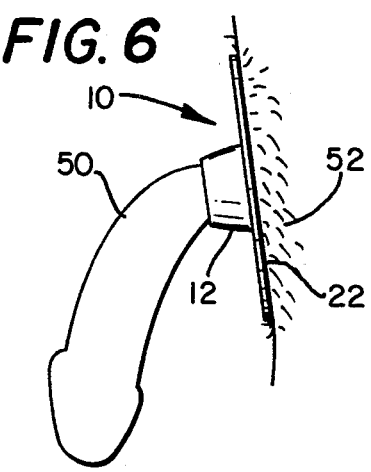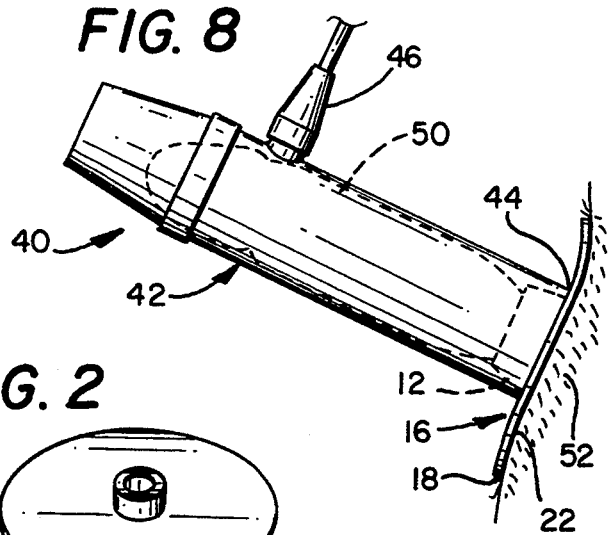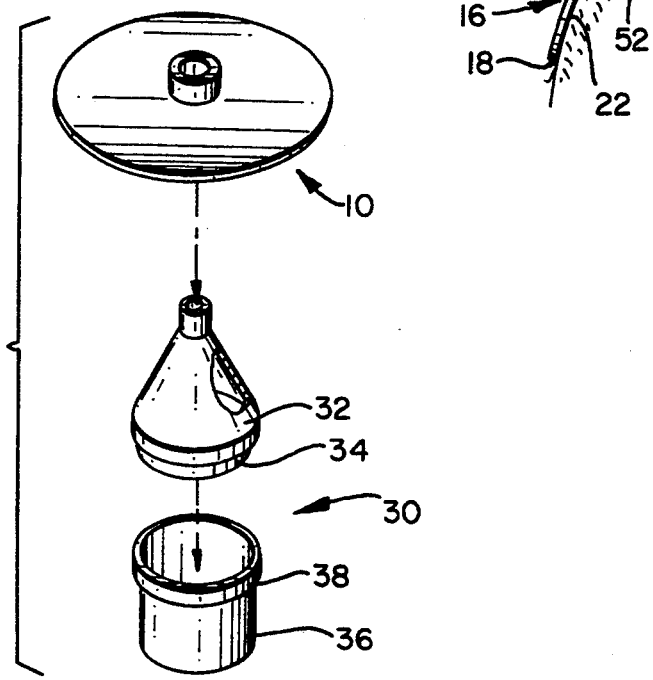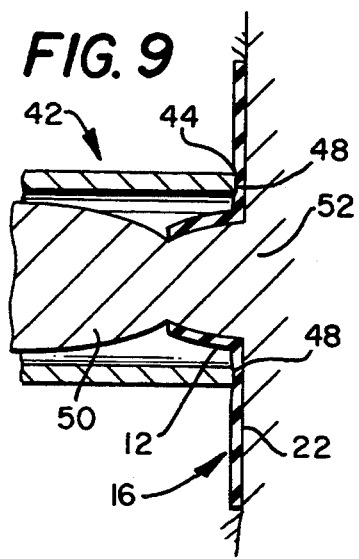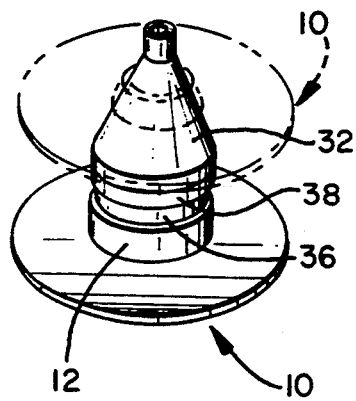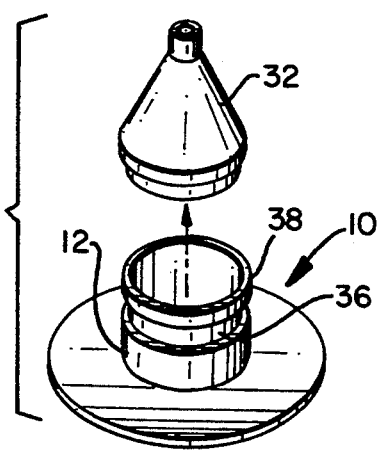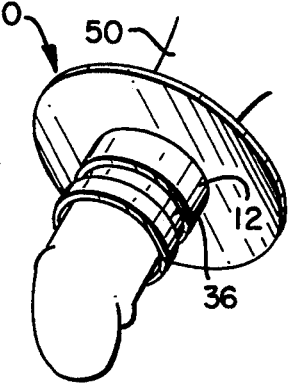

COMBINATION SEAL AND CONSTRICTING DEVICE

CROSS-REFERENCE

This application is a continuation-in-part of application Ser. No. 07/643898, filed on Jan. 22, 1991, abandoned.

TECHNICAL FIELD

This invention relates to devices used in the noninvasive treatment of impotency, and more particularly, to a combination seal and constricting device and method of use either alone or in combination with a vacuum erection device.

BACKGROUND OF THE INVENTION

For many years, surgical implantation of a penile prosthesis was a common treatment for impotence. More recently, however, non-invasive devices have been designed and prescribed for the external management of erectile dysfunction. Because of the cost and possible risks involved with surgically implanted prostheses, their use is now typically reserved for men for whom more conservative treatments have failed or proven unsuitable. External constriction devices have been provided which contract around the base of the flaccid penis and prevent the outflow of blood once the penis has risen into an erect state. Conventional constriction devices include several different styles which are best explained by three categories.

The first category encompasses external prosthetic devices which comprise large aprons or shields with elongated cylindrical sleeves. Designed to aid in the maintenance of an erection, these devices are placed over the penis and fastened to the body with ties or adhesives. Although these devices enable the user to maintain an erection, they contribute little to the user's ability to achieve a satisfactory erection. A large portion of the user's genitalia, groin and adjacent region must be covered in order for these devices to be securely fastened and function properly, resulting in the user's decreased sensitivity to intimate touching and sexual stimulation. Examples of the apron and shield devices include those disclosed in U.S. Pat. No. 1,608,806, issued Nov. 30, 1926 to Peter W. Nelson, and U.S. Pat. No. 4,872,462, issued Oct. 10, 1989 to Gilbert Salz. Such devices have not been successfully adapted for use with external erection devices.

The second category includes smaller, less cumbersome devices, known as constricting bands or rings which can be used alone or in combination with an external erection device. Once an erection is achieved, the constricting device impedes the flow of blood from the penis, keeping it in an erect state. These devices are typically made of an elastomeric material such as rubber. Constriction bands resemble conventional rubber bands and may range up to about ⅜ of an inch in width. The bands generally include an attached safety release loop made of string, thread, monofilament line, or the like, for use in placement and removal of the bands from the base of the penis.

In contrast, constriction rings generally consist of "O" rings with "C" shaped handles for ease in application and removal. By grasping the handles, the central "O" ring is stretched and placed over the base of the penis where it constricts the retraction vessels to prevent the outflow of blood. Such devices include U.S. Pat. No. 3,759,253, issued on Sep. 18, 1973 to Charles A. Cray and U.S. Pat. No. 4,539,980 issued on Sep. 10, 1985 to John L. Chaney.

When used alone, the constriction rings or bands are placed around the base of the flaccid or semi-flaccid penis, constricting the blood vessels of the penis before it is brought to an erect state. The penis is then massaged or otherwise manipulated to encourage blood flow into the penis wherein the constriction bands or rings prevent the outflow of blood and enable the user to achieve and maintain an erection.

A third category includes constriction devices specifically designed for use with suction or vacuum erection devices. Such constriction devices include a compression ring as disclosed in U.S. Pat. No. 1,225,341 issued on May 8, 1917 to Otto Lederer, a device with a short elastic sleeve as disclosed in Swiss Patent No. 347,300, granted on Jun. 30, 1960 to Guiseppi Meldi, or an elastic sleeve with an expansible diaphragm disclosed in U.S. Pat. No. 4,641,638, issued on Feb. 10, 1987 to Robert D. Perry.

The devices of the second and third categories have been used in combination with conventional, commercially available vacuum erection devices. Vacuum erection devices typically comprise an elongated evacuation cylinder, sometimes with tapered sidewalls, and are generally made of a hard, clear polymeric resin closed at one end and open at the other. The cylinder has a length and diameter sufficiently large to accommodate either a flaccid or an erect penis. Near the closed end of the cylinder, a radially extending port is provided with a fitting that is adapted to be connected by flexible tubing to a manually operable vacuum pump.

Constriction bands, rings and sleeves are provided with the vacuum erection device to be applied to the penis for the purpose of maintaining the erection achieved through use of the vacuum pump. Use of bands or rings with a vacuum erection device requires that either one ring or several bands, doubled or redoubled, be slipped over the open end of the plastic cylinder. Lubricant such as a water-soluble lubricating jelly is desirably applied to the end of the cylinder to facilitate application and removal of the bands or ring.

Once the band or ring is in place around the end of the cylinder, the cylinder is slipped over the flaccid penis and pressed against the groin. In some devices, the closed end of the cylinder is flat or textured to permit it to be braced against a stationary structure such as a table edge. This is done to assist the user in holding the cylinder firmly against the pubic bone, thereby promoting a better seal around the open end of the cylinder and simultaneously freeing the hands of the user to connect and operate the vacuum pump.

While pressing the cylinder firmly against the body around the base of the penis, the vacuum pump is operated to evacuate the cylinder. This reduction of the atmospheric pressure around the penis causes blood to engorge the penis, bringing it to an erect state.

Once erection is achieved, the constriction ring or band is slipped off the open end of the cylinder, whereupon it contracts around the base of the erect penis. Placement of the ring or band around the erect penis significantly restricts the flow of blood back out of the penis, thereby maintaining the penis in an erect state until such time as the ring or bands are removed following intimate sexual activity such as intercourse.

Removal of the bands requires the user to locate and pull the safety loops attached to the bands until the constriction device is expanded sufficiently to permit the user to grasp the bands themselves for removal from the penis. Similarly, ring removal requires the user to locate and grasp the two handles and sufficiently expand the "O" ring to permit removal from the penis.

Several disadvantages have been encountered through use of conventional constriction bands and rings either alone or with commercially available vacuum erection devices. Conventional bands become twisted when doubling them prior to placement upon the penis or when sliding them over the open end of the plastic cylinder, and are further twisted when sliding them off of the cylinder and onto the base of the erect penis, causing undesirable discomfort to the user. Often, pubic hair becomes intertwined with the ring or bands as they are slipped off the cylinder and contracted around the base of the penis which can be very painful to the user during intimate activity and removal. The safety loops attached to the bands can also become wrapped in the bands and pubic hair, making them difficult for the user to grasp during the removal process. When a user has difficulty removing a ring or bands, the user must pull the constricting device away from the penis and cut it with scissors or a knife, taking precautions to avoid injury.

Moreover, because conventional bands, rings and sleeves are not flush against the open end of the evacuation cylinder and do not conform to the surface area of the user's groin, they do not assist in establishing or maintaining an airtight seal around the open end of the vacuum cylinder during evacuation. Since the surfaces of existing constriction devices such as those disclosed in Cray, Chaney, Lederer, Meldi, and Perry fail to provide an air-tight seal between the open end of the cylinder and the constricting device during pumping and evacuation, the effectiveness of the vacuum cylinder for creating a satisfactory penile erection is significantly reduced.

Prior art, such as the Cray and Chaney constriction rings, Lederer compression rings or the Meldi and Perry sleeves do not contain any disclosure or teaching of their use or adaptability as a combination seal and constricting device. The constriction rings of the Cray and Chaney devices, with either a trefoil or circular opening, and the Lederer compression ring, composed of a plurality of disconnectable thin disks, do not have a seating surface adaptable to conform to the user's groin and the open end of the vacuum cylinder to provide an airtight seal.

Although the constriction device disclosed in Meldi is specifically designed for use with a vacuum erection device, it too lacks the means for effectively creating an air-tight seal. A circular device with a short sleeve, it is held in place inside the open end of the cylinder with two small tabs that fold over the outer edge of the cylinder. With no means to create an air-tight seal around the circumference of the open end of the cylinder, such as skirt radially extended beyond the circumference of the open end of the vacuum cylinder, the tabs merely serve to prevent the constricting device from slipping out of position during operation of the vacuum erection device.

The inherent nature of the expansible diaphragm sleeve disclosed in Perry provides a changing wall thickness and sloped, tapered skirt which does not conform to the user's groin area or the circumference of the evacuation cylinder. In this case, the inherent gaps caused by the sloped and tapered skirt prevent the user from establishing an airtight seal around the open end of the evacuation cylinder.

A new means is therefore needed that will safely and comfortably serve as a combination seal and constricting device. Such a means is provided herein.

SUMMARY OF THE INVENTION

According to the present invention, a combination seal and constricting device and method of use is provided for the external treatment of impotency, either alone or in combination with a vacuum erection device.

According to a preferred embodiment of the invention, a system for the treatment of erectile dysfunction is provided that preferably comprises a vacuum erection device in combination with a combined seal and constricting device.

According to a preferred embodiment of the invention, the combination seal and constricting device is made of a pliable elastomeric material and comprises a centrally disposed cylindrical collar connected at one end thereof to a radially extending skirt.

According to another preferred embodiment of the invention, the combination seal and constricting device includes a raised skirt edge.

According to another preferred embodiment of the invention, the combination seal and constricting device includes arcuate ribs spaced radially outward from the center of the device;

According to another preferred embodiment of the invention, the combination seal and constricting device includes two sets of arcuate ribs positioned substantially opposite each other and spaced radially outward from the center of the device.

According to another preferred embodiment of the invention, a method of use to stimulate and maintain the penis in an erect state is provided that comprises the steps of placing the combination seal and constricting device over the user's flaccid or semi-flaccid penis so that its skirt conforms flush against the user's groin; placing a vacuum erection device over the user's flaccid penis so that the open end of the vacuum cylinder rests flush against the smooth portion of the outwardly facing elastomeric seating surface of the radially extending skirt; pressing the vacuum cylinder against the seating surface so that the circumference of the open end of the cylinder pushes into the seating surface of the radially extending skirt to create an air-tight seal between the cylinder and constricting device; activating the evacuation cycle of the vacuum erection device until the user has achieved the desired erect state; releasing the vacuum created by the evacuation cycle; and withdrawing the vacuum erection device from the constricting device and the erect penis.

BRIEF DESCRIPTION OF THE DRAWINGS

The apparatus of the invention is further described and explained in relation to the following figures of the drawings in which:

FIG. 2 is an exploded perspective view of the combination seal and constriction device of the invention and an applicator assembly;

FIG. 3 is a front perspective view of the applicator assembly as assembled with the combination seal and constricting device stretched over the applicator assembly from the initial position shown with the phantom lines to the final position shown with the solid lines at the base of the applicator assembly;

FIG. 4 is an exploded perspective view of the applicator assembly device after the combination seal and constricting device has been installed and applicator cone has been removed from the applicator sleeve;

FIG. 5 is a front perspective view of the combination seal and constricting device and applicator sleeve which depicts its placement over a flaccid penis;

FIG. 6 is a simplified side elevation view of the combination seal and constricting device after it has been placed over a flaccid penis and the applicator sleeve has been removed;

FIG. 8 is a simplified side elevation view depicting the cylindrical collar of the combination seal and constricting device of the invention positioned within the open end of the plastic cylinder portion of a vacuum erection device with the skirt resting between the circumference of the open end of the cylinder and the user's groin;

FIG. 9 is a cross-sectional side elevation side view depicting the seal created between the open end of the cylinder and the combination seal and constricting device;

DESCRIPTION OF THE PREFERRED EMBODIMENT

Figure 1:
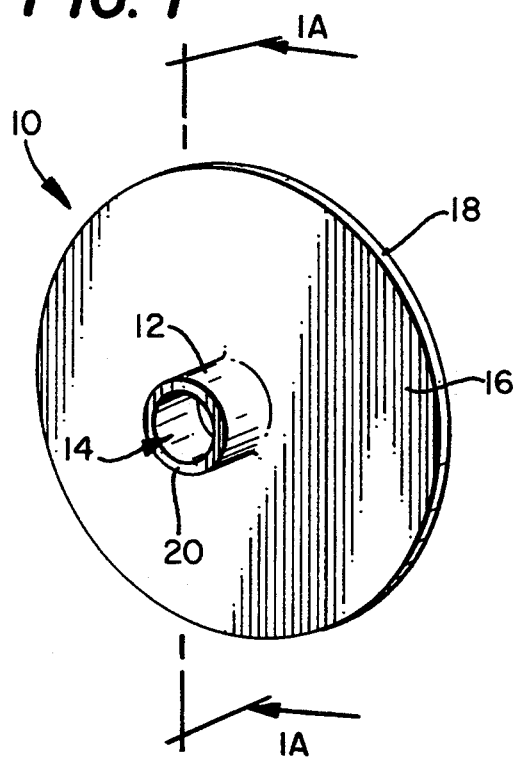
FIG. 1 is a front perspective view of the combination seal and constricting device of the invention.

Referring to FIGS, 1, 1A, and 10, combination seal and constricting device 10 of the invention is preferably made of a moldable, pliable, elastomeric material (such as a synthetic rubber) selected from the many such conventional materials that are commercially available. Device 10 is preferably unitarily molded as a single piece. Device 10 preferably comprises a substantially cylindrical collar 12 defining cylindrical aperture 14 therethrough. Radially extending skirt 16 is preferably concentrically disposed around cylindrical collar 12, and is desirably molded flush with the end of cylindrical collar 12 that is opposite collar edge 20.

According to a preferred embodiment of the invention, elastomeric seating surface 24 extends radially outward to edge 18 of skirt 16 from cylindrical collar 12 a sufficient distance to permit skirt 16 to be easily grasped by the user during application to or removal from the penis.

Figure 10:
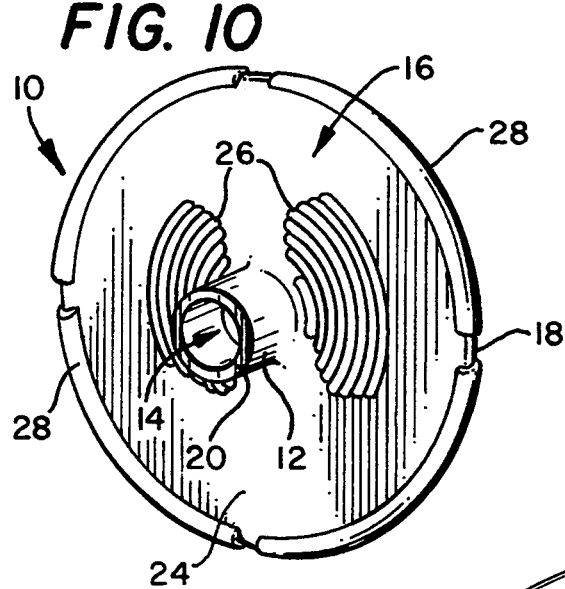
FIG. 10 is a front perspective view of another embodiment of the combination seal and constricting device of the invention having two diametrically opposed sets of arcuate ribs disposed radially outward from the cylindrical collar of the device and inwardly from the raised skirt edge a sufficient distance to permit the open end of a vacuum cylinder to seat against the skirt between the ribs and the skirt edge.
Figure 11:
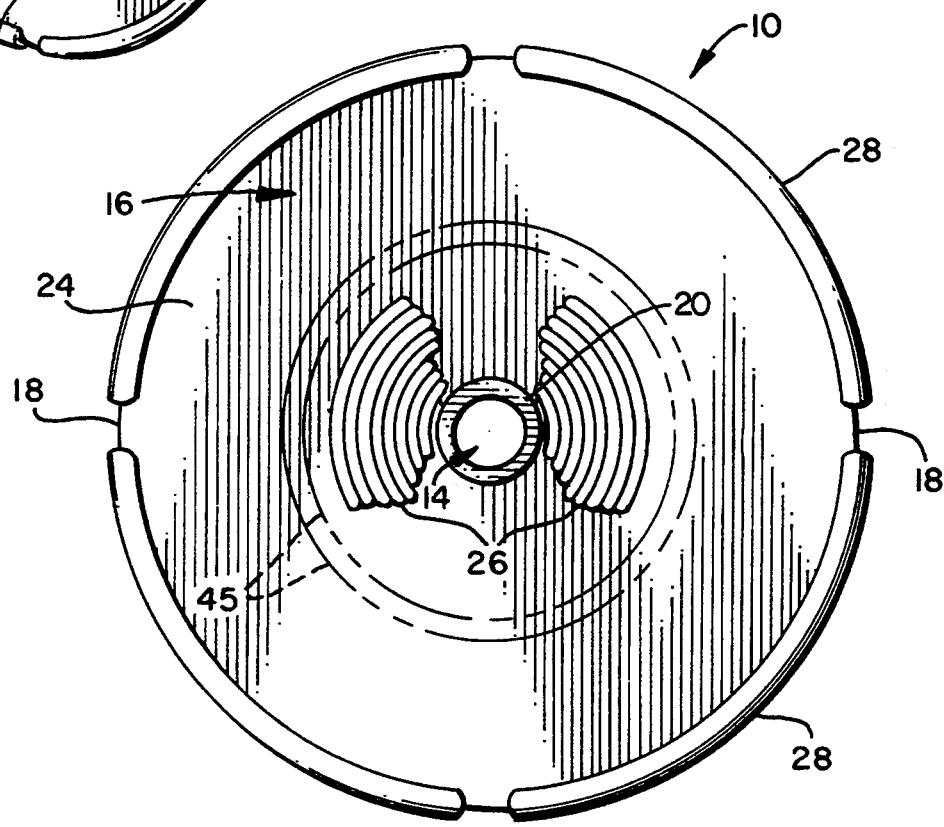
FIG. 11 is a front elevation view of the combination seal and constricting device of the invention depicting two circular phantom lines radially spaced beyond the arcuate ribs to indicate preferred placement of the open end of the vacuum cylinder in relation to the arcuate ribs and the skirt edge.
Figure 12:
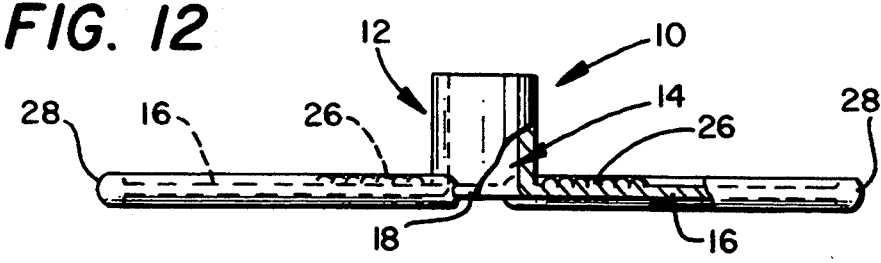
FIG. 12 is a cross-sectional side elevation view of the combination seal and constricting device of the invention depicted in FIG. 10.

Referring to FIGS. 10, 11 and 12, the application and removal of device 10 of the invention may be aided by including raised sections 28 along edge 18 of skirt 16 and arcuate ribs 26 spaced radially outward from cylindrical collar 12 on elastomeric seating surface 24. In this preferred embodiment, arcuate ribs 26 and raised sections 28 provide an uneven, raised surface between the user's thumbs and elastomeric seating surface 24, enabling the user to maintain a firm grip on device 10 for quick, easy removal without undue slippage.

Referring to FIG. 6, device 10 is placed over the user's flaccid or semi-flaccid penis 50 so that collar 12 encircles the shaft of the penis and the rearwardly facing surface 22 of skirt 16 rests flush against the user's groin 52. After the user has completed the desired intimate activities, the user easily removes device 10 by grasping edge 18 and surface 24 of skirt 16 and sliding device 10 off the head of penis 50.

Referring to FIGS. 1 through 6, device 10 may be applied to user's penis 50 with the aid of an applicator assembly 30. As shown in FIG. 2, applicator assembly 30 preferably comprises an applicator cone 32 with a cone base 34 and an applicator sleeve 36 with a sleeve lip 38. To use applicator assembly 30, base 34 of cone 32 is set into lip 38 of sleeve 36. Referring to FIG. 3, device 10 is positioned over the top of cone 32 and pushed down cone 32 until it rests securely around sleeve 36. Once device 10 is in position, cone 32 is removed. As shown in FIG. 5, sleeve 36 and device 10 are placed over the head of user's penis 50 so that it encircles the penis 50 and rests against the user's groin 52. Holding the constricting device 10 in position at the base of the user's penis 50, the applicator sleeve is withdrawn from aperture 14 of collar 12 and removed from penis 50 so that device 10 is positioned as shown in FIG. 6. Because skirt 16 is pliable, it conforms easily to the physiology of the user.

Figure 7:
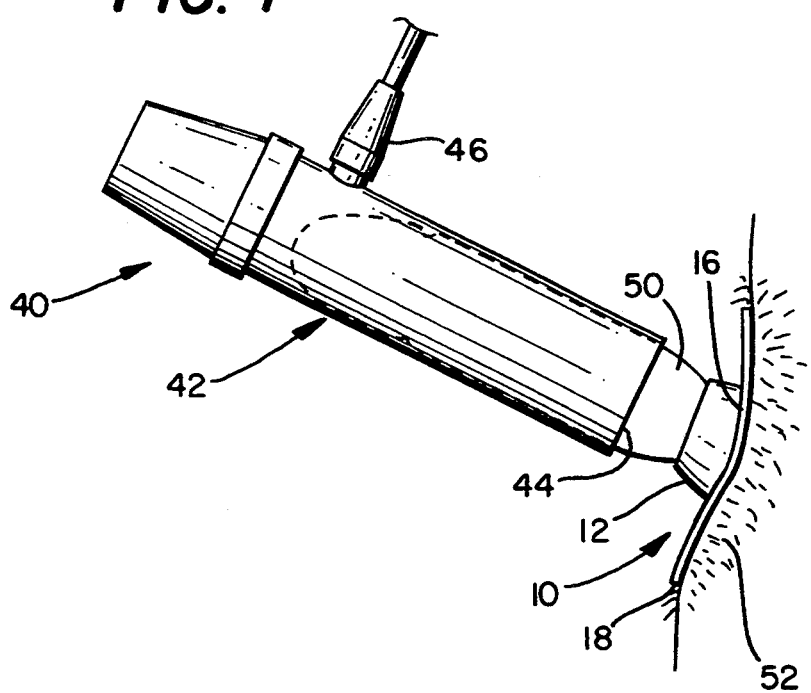
FIG. 7 is a simplified side elevation view depicting the combination seal and constricting device positioned around the base of an erect penis with the cylinder of the vacuum erection device being slipped over the penis.

Once device 10 is in position as shown in FIG. 6, the penis is preferably brought to an erect state by use of an external device such as a conventional vacuum erection device. Referring to FIGS. 7, 8 and 11, a vacuum erection device 40 is placed over penis 50 so that the circumference of open end 44 of the evacuation cylinder 42 rests flush against elastomeric seating surface 24 of skirt 16. Skirt 16 radially extends a sufficient distance beyond the circumference of open end 44 so that it is not pulled into cylinder 42 during the evacuation cycle. Referring to FIG. 9, vacuum erection device 40 is preferably pressed toward the user's groin so that the circumference of open end 44 pushes into seating surface 24 of skirt 16, causing depression 48 thereby creating an airtight seal between cylinder 42 and the combination seal and constricting device 10. Vacuum erection device 40 is then evacuated through fitting 46 until penis 50 is in the desired erect state. Evacuation cylinder 42 is then removed from penis 50 and device 10 stays securely positioned around the base of penis 50 while the user engages in the desired intimate activities. Upon completion of the desired activities, device 10 is removed by grasping edge 18 of skirt 16 and sliding device 10 over the head of penis 50. Referring to FIG. 11, in another preferred embodiment of the invention, the circumference of open end 44 of evacuation cylinder 42 is seated on surface 24 radially beyond arcuate ribs 26 but well inside edge 28.

When used with a vacuum erection device 40, device 10 aids in establishing and maintaining a substantially airtight seal around the open end of cylinder 42 and the base of the penis 50 during evacuation. Because of its configuration, device 10 does not twist or pull pubic hair either during application to or removal from the penis, and provides a comfortable, safe, effective way of achieving and maintaining the desired erect state.

Referring to FIGS. 1 through 12, when cylindrical collar 12 is in its relaxed, unexpanded state, it preferably has an outside diameter of about 1.4 cm, an inside diameter of about 0.84 cm, and extends perpendicularly outward from skirt 16 a distance of about 1.6 cm. Cylindrical collar 12 and aperture 14 are preferably centrally disposed relative to outside edge 18 of skirt 16, which in the embodiment shown, has a diameter of about 10.2 cm. The thickness of skirt 16 is preferably about 0.15 cm, the thickness of the sidewall of cylindrical collar 12 is preferably about 0.28 cm, and the thickness of beads 28 are preferably about 0.32 cm. It should be understood that such exact proportions are not critical to the invention, and can be varied according to factors such as, for example, the elasticity of the material used in making device 10. In general, a cylindrical collar having a length ranging from 0.5 to about 1.2 times its external diameter when in a relaxed, unexpanded state is preferred for use in the invention. Cylindrical collar 12 should be expandable to a maximum diameter greater than that of applicator sleeve 36 or any other applicator with which is it used, which is ordinarily about two inches or less. The diameter of collar 12 is preferably not so large, however, that collar 12 will not contract a sufficient amount to properly constrict around penis 50. The diameter of cylinder 42 should likewise be slightly larger than the diameter of penis 50 when penis 50 is fully erect.

Figure 1A:
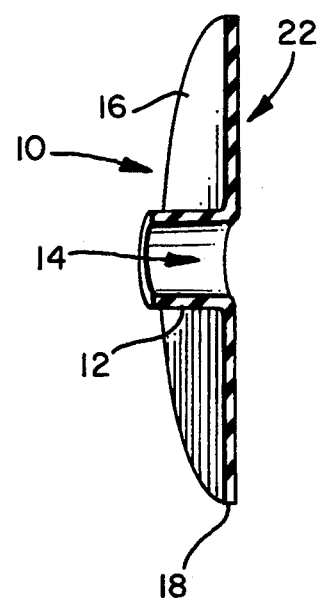
FIG. 1A is a front perspective view of the combination seal and constricting device of the invention with a section taken along line 1A—1A of FIG. 1.

Referring to FIGS. 1, 1A, and 10, cylindrical aperture 14 in cylindrical collar 12 should have a minimum diameter when in its relaxed, unexpanded state that is smaller than the diameter of the erect penis 50 with which is it to be used, but large enough to avoid unduly constricting penis 50. Although it is believed that most erect adult penises can be accommodated with a single, properly sized device 10, a plurality of devices 10 having collars 12 with cylindrical apertures 14 of differing diameters can be provided to best accommodate the erect penis size of a particular user.

Referring to FIGS. 10 through 12, according to another preferred embodiment of the invention, a plurality of arcuate ribs 26 are disposed on opposite sides of cylindrical collar 12 to facilitate manual grasping of the skirt during application or removal of device 10 without interfering with sealing engagement between the skirt and vacuum cylinder. Each of the ribs is preferably about 0.16 cm wide and 0.1 cm high.

While the apparatus of the invention is described herein in relation to its preferred embodiments, it is understood that other alterations and modifications of the invention will become apparent to those of ordinary skill in the art upon reading this disclosure, and it is intended that the scope of the invention be limited only by the broadest interpretation of the appended claims to which the inventor is legally entitled.

We claim:

1. A combination seal and constricting device adapated for use in the external treatment of erectile dysfunction, comprising a substantially cylindrical elastomeric collar having a diameter expandable to accommodate a penis and a radially extending skirt having a forwardly facing, annular, elastomeric seating and sealing surface, a rearwardly facing surface substantially flush with one end of said collar, and a skirt edge, said skirt having a circumference and a radius extending from said collar to said skirt edge, the radius being substantially greater than the unexpanded collar diameter around the entire circumference.

2. The device of claim 1 wherein said collar and said skirt are unitarily molded.

3. The device of claim 1 wherein said skirt further comprises beads evenly spaced around the circumference of said skirt edge.

4. The device of claim 1 wherein said skirt further comprises arcuate ribs disposed radially outward from said collar.

5. The device of claim 4 further comprising at least two sets of ribs disposed diametrically opposite the collar.

6. The device of claim 1 wherein said collar has a height and diameter, with the height ranging from about 0.5 to about 1.2 times the diameter.

7. The device of claim 1 wherein said collar has a height and diameter which are about equal.

8. The device of claim 1 wherein said cylindrical collar has a height of about 1.6 cm.

9. The device of claim 1 wherein said collar has an unexpanded outside diameter of about 1.4 cm. and defines an aperture having an unexpanded inside diameter of about 0.84 cm that is expandable to a diameter of about 5 cm.

10. The device of claim 1 where, in the unexpanded state, the radius of said skirt extends about 4.2 cm from said collar to said skirt edge.

11. A combination seal and constricting device adapted for use with a vacuum erection device for the external treatment of erectile dysfunction, comprising a substantially cylindrical elastomeric collar having a diameter expandable to accommodate a penis and a radially extending skirt having a forwardly facing, annular, elastomeric seating and sealing surface, a rearwardly facing surface substantially flush with one end of said collar, and a skirt edge, said skirt having a circumference and a radius extending from said collar to said skirt edge, the radius being substantially greater than the collar diameter around the entire circumference.

12. The device of claim 11 wherein said skirt further comprises beads evenly spaced around the circumference of said skirt edge.

13. The device of claim 11 wherein said skirt further comprises at least two sets of arcuate ribs on said seating and sealing surface disposed radially outward from said collar to a distance less than half said skirt radius.

14. A method for using the combination seal and constricting device of claim 11 with a vacuum erection device which comprises a vacuum cylinder with an open end, comprising the steps of:
   a. placing said constricting device over a user's flaccid penis so that said constricting device encircles said penis and said rearwardly facing surface of said skirt rests flush against a user's groin;
   b. positioning said vacuum cylinder over said penis so that said open end rests flush against said elastomeric seating surface of said skirt;
   c. pressing said vacuum cylinder toward said groin so that said open end pushes into said seating surface of said skirt creating an airtight seal between said cylinder and said combination seal and constricting device;

d. operating said vacuum erection device until said penis is in the desired erect state; and e. withdrawing said vacuum erection device from said erect penis.

15. A system for the treatment of penile erectile dysfunction, comprising:

a. a vacuum cylinder;

b. an elastomeric combination seal and constricting device, comprising:

(1) elastomeric self constricting means for constricting the penis;

(2) pliable elastomeric seal means extending radially outward from said constricting means for providing a continuous annular seating and sealing surface area for said cylinder around said constricting means; and (3) circumferentially extending skirt means extending radially outward substantially beyond said annular seating and sealing surface area.

16. The system of claim 15 further comprising an applicator assembly wherein said applicator assembly comprises an applicator cone and an applicator sleeve.

17. The system of claim 15 wherein said constricting means comprises a substantially cylindrical elastomeric collar having a diameter expandable to accommodate said penis.

18. The system of claim 15 wherein said skirt means comprises an edge and beads evenly spaced around the circumference of said edge.

19. The system of claim 15 wherein the combination seal and constricting device comprises at least two sets of diametrically opposed arcuate ribs, 20. The system of claim 19 wherein said annular seating and sealing surface area extends radially outward from said arcuate ribs.

* * * * *